United States Patent [19]

Spencer

[11] Patent Number: 4,610,670
[45] Date of Patent: Sep. 9, 1986

[54] STERILE CONNECTION PROCESS, APPARATUS AND SYSTEM

[75] Inventor: Dudley W. C. Spencer, Wilmington, Del.

[73] Assignee: E. I. Du Pont de Nemours and Company, Wilmington, Del.

[21] Appl. No.: 599,324

[22] Filed: Apr. 12, 1984

Related U.S. Application Data

[63] Continuation-in-part of Ser. No. 503,657, Jun. 13, 1983, abandoned.

[51] Int. Cl.$^4$ ................................................ A61M 1/00
[52] U.S. Cl. ...................................... 604/29; 604/410; 604/905
[58] Field of Search ................ 604/29, 244, 280, 283, 604/905; 156/152, 158, 159, 296, 502, 503, 251, 358, 304.2, 304.3, 304.5, 433

[56] References Cited

U.S. PATENT DOCUMENTS

| | | | |
|---|---|---|---|
| 2,805,973 | 5/1954 | Klasing et al. | 154/83 |
| 2,936,816 | 5/1960 | Lang | 154/42 |
| 3,013,925 | 12/1961 | Larsen | 156/153 |
| 3,035,631 | 5/1962 | Knowles | 156/579 |
| 3,117,903 | 1/1964 | Hix | 156/158 |
| 3,897,296 | 7/1975 | Waldrum | 156/158 |
| 3,968,195 | 7/1976 | Bishop | 264/154 |
| 4,022,256 | 5/1977 | Berkman et al. | 141/1 |
| 4,157,723 | 6/1979 | Granzow et al. | 141/1 |
| 4,209,013 | 6/1980 | Alexander et al. | 128/213 A |
| 4,219,221 | 8/1980 | Webb | 604/244 |
| 4,223,675 | 9/1980 | Williams et al. | 128/272 |
| 4,242,310 | 12/1980 | Greff et al. | 422/300 |
| 4,253,500 | 3/1981 | Williams | 141/1 |
| 4,255,222 | 3/1981 | Guenther | 156/433 |
| 4,288,266 | 9/1981 | Konrad et al. | 156/304.2 |
| 4,369,779 | 1/1983 | Spencer | 128/213 A |
| 4,412,835 | 11/1983 | Spencer | 604/905 |
| 4,443,215 | 4/1984 | Smith | 604/905 |
| 4,501,630 | 2/1985 | Kiuchi | 156/304.3 |
| 4,507,119 | 3/1985 | Spencer | 604/905 |

FOREIGN PATENT DOCUMENTS 2250130  4/1974  Fed. Rep. of Germany .

OTHER PUBLICATIONS

Myhre et al., "An Aseptic Fluid Transfer System for Blood and Blood Components", Transfusion, 18, pp. 546–552 (1978).

Primary Examiner—John D. Yasko
Assistant Examiner—Michelle N. Lester

[57] ABSTRACT

A process, apparatus and system for making a sterile connection between thermoplastic resin tubes is disclosed. A section of each tube is flattened and a hot cutting means is urged through the flattened sections so as to seal temporarily each tube and to provide molten tube ends. The tubes are aligned with each other and then the desired molten tube ends are urged together to form a joint between the tubes for each pair of tube ends to be connected. Each joint is cooled and then subjected to light stress to open the temporary seal in each tube, thereby providing fluid communication between the joined tubes.

40 Claims, 25 Drawing Figures

F I G. 6
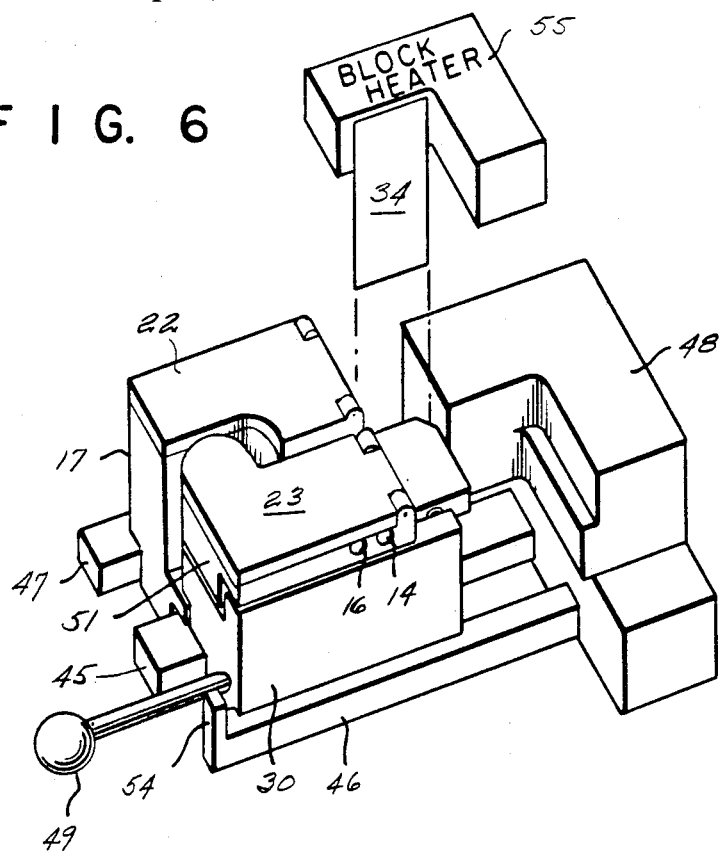
F I G. 7
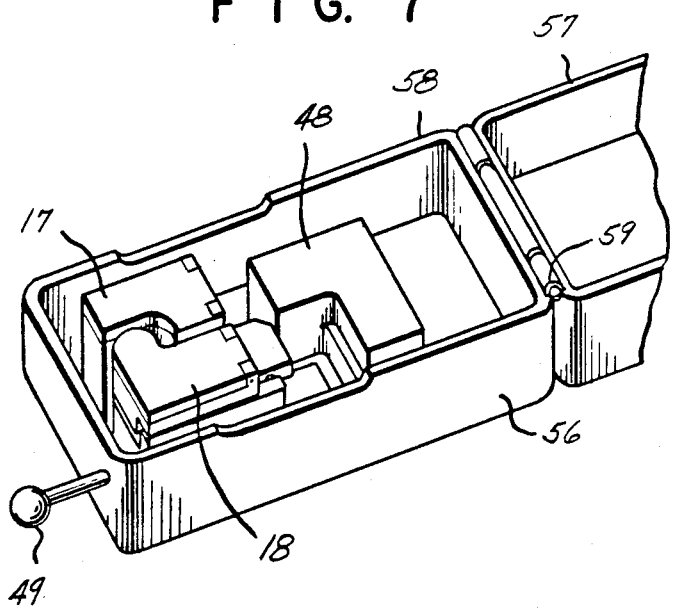

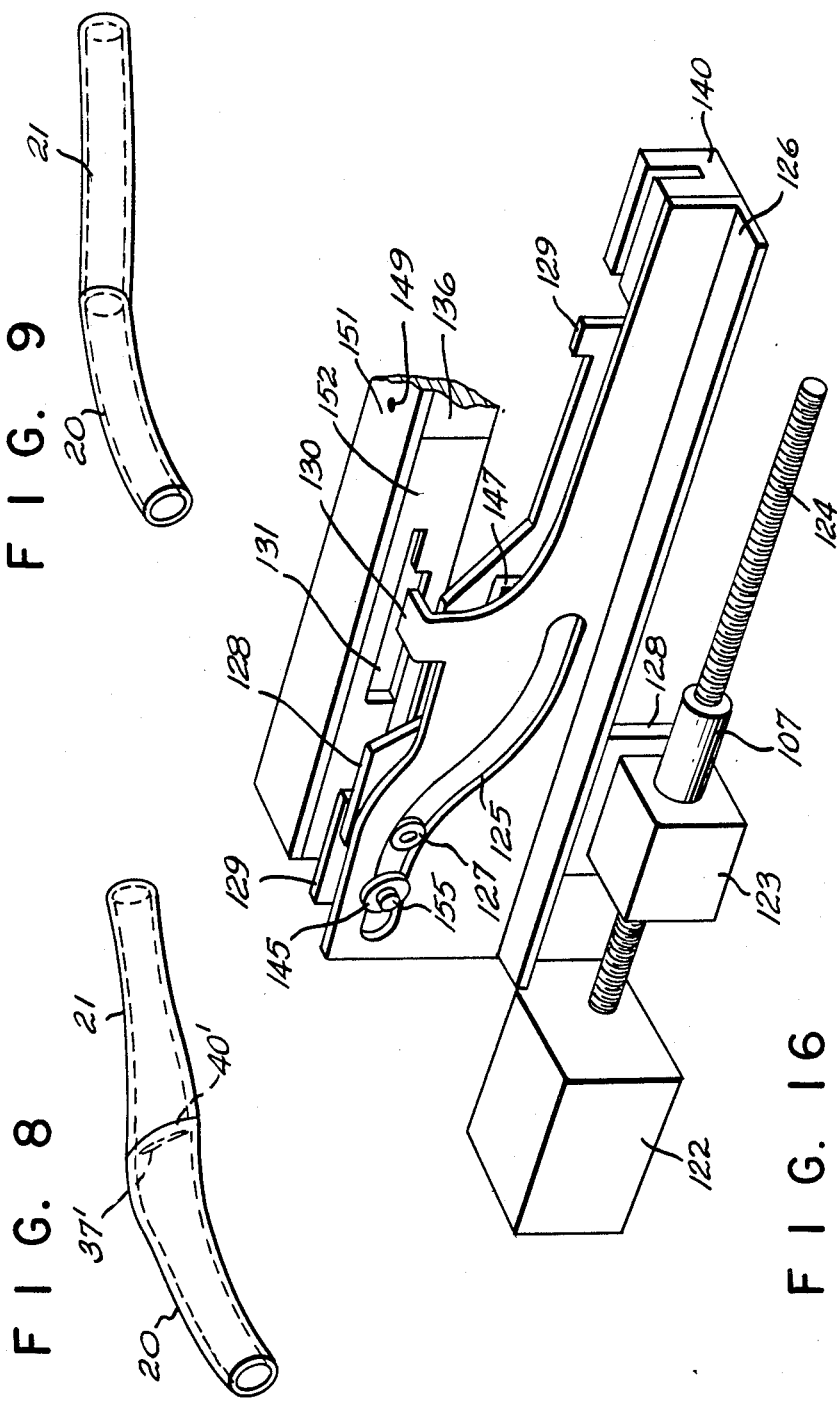

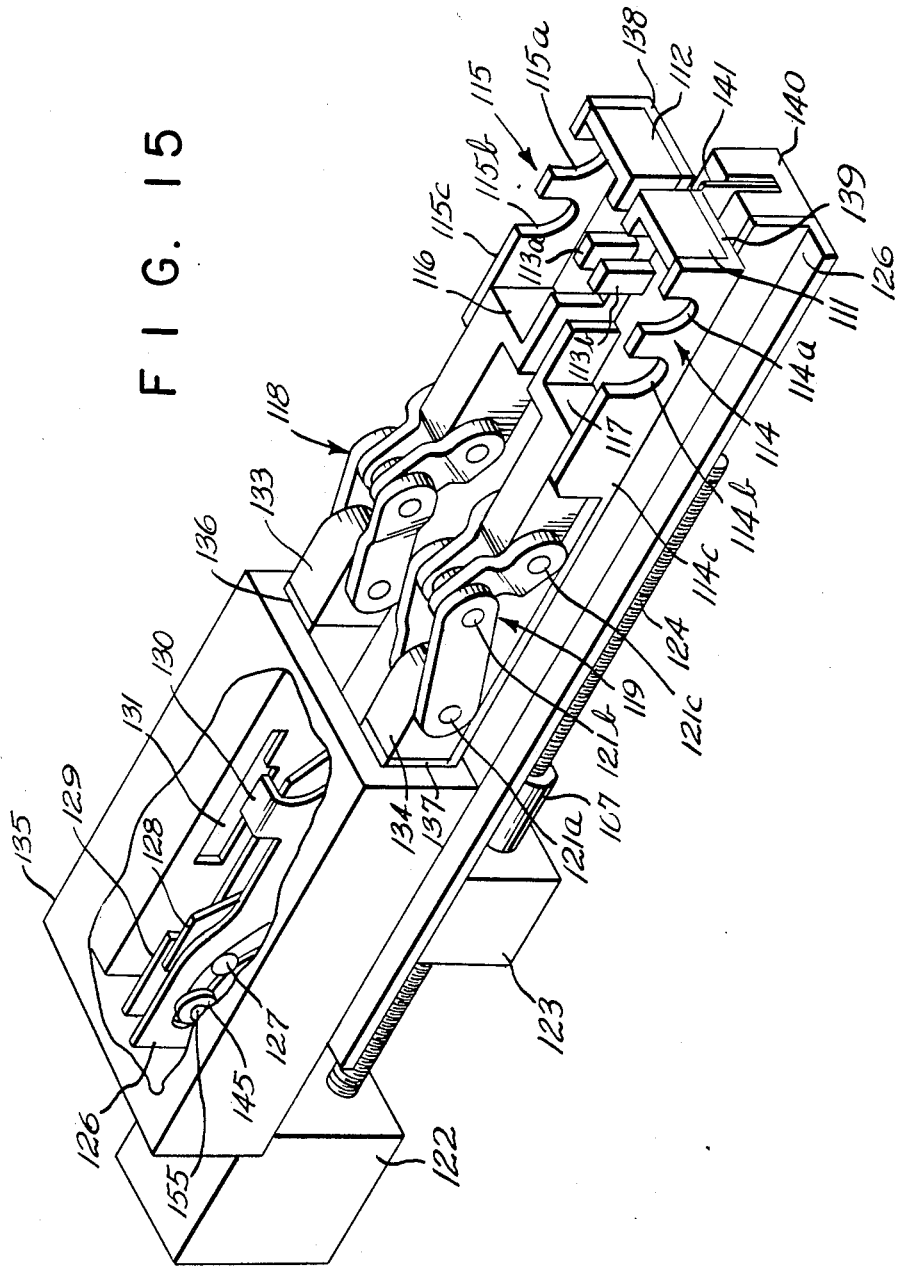

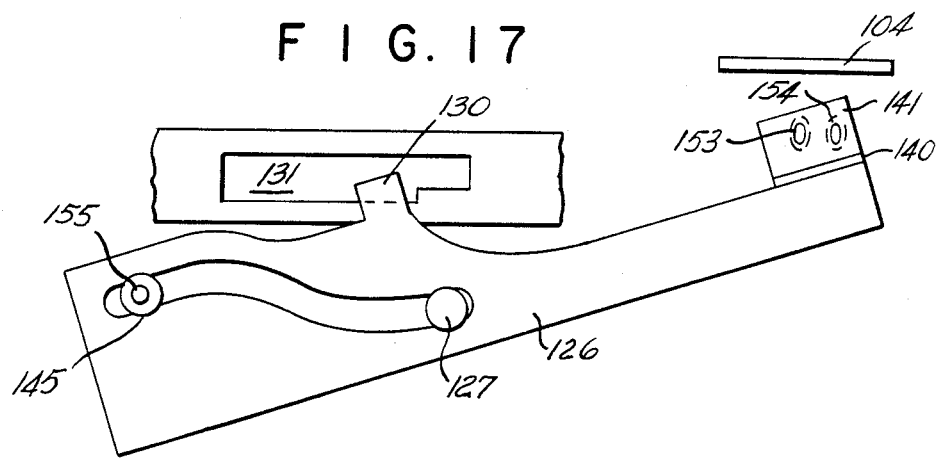
FIG. 17
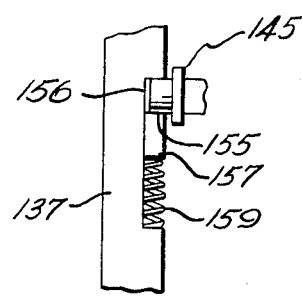
FIG. 18
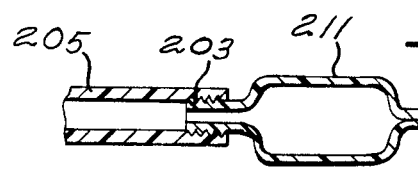
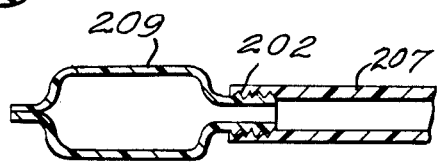
FIG. 23
FIG. 24
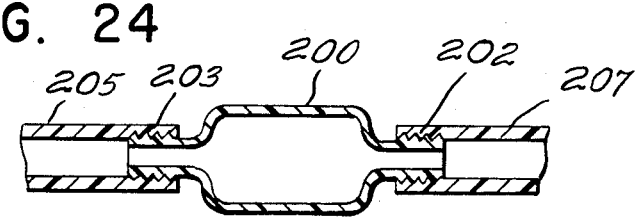

4,610,670

STERILE CONNECTION PROCESS, APPARATUS AND SYSTEM

CROSS-REFERENCE TO RELATED APPLICATIONS

This application is a continuation-in-part of copending application Ser. No. 503,657, filed on June 13, 1983 now abandoned.

BACKGROUND OF THE INVENTION

1. Field of the Invention

This invention relates to a process, apparatus and system for forming a sterile connection (sterile docking) between two tubes.

At the present time there are a number of medical and scientific procedures which require the sterile transfer of fluids from one container to another. The only truly sterile transfer system in current commercial use involves prejoining containers with tubes and then sterilizing the entire assembly. This is inflexible and costly since new containers cannot be added and the number of joined containers needed is often not known at the time of initial filling.

An example of the need for sterile docking is in continuous ambulatory peritoneal dialysis (CAPD). This procedure is replacing dialysis of blood outside the body in membrane diffusion cells where waste products normally removed by kidneys are washed from the blood, which is then returned to the patient. Dialysis outside of the body is a time-consuming procedure and sometimes results in damage to the blood by exposure to materials and conditions external to the body. In CAPD, the patient is required to spend time only for draining spent dialysate and replacing it with a fresh solution.

The CAPD patient has a tube connected to his or her peritoneal cavity via an implanted catheter. A tube from a bag of fresh dialysis solution is connected to the patient's tube. The fresh dialysis solution is drained from the bag into the patient's peritoneal cavity where it remains for about 3-4 hours. During this treatment period, the empty bag is folded and carried by the patient who can continue with his or her normal activities. After this treatment period, the spent dialysate is drained back into the empty bag which is then disconnected from the patient's tube. A bag of fresh dialysis solution is then connected to the patient's tube and the procedure is repeated. Connection to a new bag of dialysis solution exposes the tube ends to airborne bacteria or other contamination even though precautions are taken. Prior to the invention disclosed in U.S. Pat. No. 4,369,779, no satisfactory way has existed to insure sterility in spite of the elaborate and costly precautions employed including the use of masks, gloves, gauze strips and disinfectant solutions. Usually with methods now commercially available contamination occurs to the extent that a case of peritonitis is contracted perhaps on the average once or more a year and scar tissue from it inhibits dialysis.

Truly sterile connections could minimize the occurrence of peritonitis. Also any other treatment bags, such as for an antibiotic, bacteriostat, or other medication, could be connected as desired.

A similar need for sterile connection exists for blood bags. At present, blood from a donor is drawn into a primary bag which may be joined to one or two satellite bags, all connected and sterilized before use. These satellite bags may be needed for holding blood separated components, such as plasma or platelets; treating agents, such as bases, buffers, stabilizers for cell metabolism, other preservatives, or rejuvenants; or washes to remove a treating agent or other contaminant. Actually, it is not feasible to have preconnected bags for all the treatments which may be desired. Prior to the invention disclosed in U.S. Pat. No. 4,369,779, supplemental treatments such as fresh preservative could not be added sterilely during bag storage by any commercially acceptable procedure. In addition, to avoid the expense of unused satellite bags, the number of such bags is chosen based on limited, predicted needs. The inability to forecast needs well adds greatly to inventory requirements and complicates scheduling of blood donations.

Currently, very limited use is made of quality control as a time assay of the quantity and quality of components in separated blood factions. The main reason for the current limited use is that heretofore, using methods commercially available, any entry into a sterile blood unit exposed the blood to bacteria, thereby requiring that the blood be used within 24 hours from entry. Hence, although the viability of stored blood components can be extended by supplemental treatments, such as adding a preservative during storage, such treatments are usually not effected.

Moreover, the primary blood bag contains anticoagulant which can be sterilized only by heat (steam); thus all preconnected bags are also sterilized by wet-sterilization techniques, i.e., steam or hot water in an autoclave apparatus. These bags are made of plasticized polyvinyl chloride (PVC), although other materials are known to be useful for constructing bags which are favorable for other reasons, such as greater oxygen permeability. Since many such materials, e.g., oxygen permeable polyethylene, are not steam sterilizable, they are not now used in preconnected systems.

A sterile connection means would permit one to effect whatever processing is desired without compromising sterility, limiting storage life or requiring the preconnection of a multitude of bags, all wet-sterilizable, without knowing which, if any, will be used.

2. References

U.S. Pat. No. 3,013,925, issued to Larsen on Dec. 19, 1961, discloses a method of welding two joints of thermoplastic pipe wherein the inside of each end of the joints of pipe to be welded is beveled and the ends of the pipes are heated, for example by pressing the ends of the sections of pipe against a heated plate, after which the ends of the sections are forced together so that flow of softened material is to the outside of the pipe and a weld is effected substantially without formation of a bead on the inside of the welded pipe.

U.S. Pat. No. 3,035,631, issued to Knowles on May 22, 1962, discloses a tip for welding plastic parts. The tip has a knife edge at each of two opposing ends. One end of the knife is thick whereas the other is thin. The patent states that as the thin end passes through the joint, it will induce molten plastic surfaces to flow together.

U.S. Pat. No. 3,117,903, issued to Hix on Jan. 14, 1964, discloses a method of joining thermoplastic pipe without forming a troublesome inside ridge at the point of weld. The ends of the pipe to be welded are immersed in a hot bath of an inert high boiling organic liquid to cause the ends to expand and flare outwardly so that when the pipe is withdrawn from the bath and the ends butted together, the polymer in the two sections of pipe fuses together without forming a troublesome ridge.

U.S. Pat. No. 3,897,296, issued to Waldrum on July 29, 1975, discloses a method of welding two plastic surfaces together by juxtapositioning the surfaces, heating the surfaces to a temperature approaching the flash point of the plastic surfaces to liquefy the surfaces, removing a portion of the liquefied surfaces to expose unoxidized surfaces therebeneath and immediately bringing the unoxidized surfaces into abutment with one another. The patent is silent as to cutting a tube as well as forming a sterile dock.

U.S. Pat. No. 3,968,195, issued to Bishop on July 6, 1976, discloses a method for making a sterile connection between two rigid tubes the free ends of which have thermoplastic diaphragms which seal off the free ends. When a sterile connection between the free ends of the two tubes is desired, the free ends of each rigid tube are aligned while being spaced slightly apart, and each thermoplastic diaphragm is opened by heating. The free ends of the rigid tubes are then brought into contact and held in position under a slight pressure while the thermoplastic material cools and solidifies, thereby creating a permanent connection. This process requires tubes which have low-melting thermoplastic diaphragms on the ends which can only be used once, i.e., another connection to the same tubing cannot be made.

U.S. Pat. No. 4,209,013, issued to Alexander et al. on June 24, 1980, discloses an improvement in a sterile connector system for continuous peritoneal dialysis in which a dialysis solution container having a transfer port is coupled to tubing extending from a patient's peritoneal cavity. The improvement comprises a flexible housing having a first area thereof for attachment to the transfer port and a second spaced area for attachment to the patient's tubing. The attachment areas define openings for enabling the transfer port and patient's tubing to extend within the interior of the flexible housing when they are attached thereto. The flexible housing has means for receiving a sterilizing fluid therein and is operable to enable the transfer port and the patient's tubing to be sterilized within the housing and also connected to each other within the housing.

U.S. Pat. No. 4,223,675, issued to Williams on Sept. 23, 1980, discloses a system for producing sterile, nonautoclavable body fluid containers having autoclaved liquid therein, comprising a dry-sterilized package formed of a material which is unsuitable for being subjected to autoclave conditions, said dry-sterilized package including a sterile communication with the interior of said package; an autoclavable dispenser constructed of an autoclavable substance and containing liquid which was sterilized within the dispenser, said dispenser including a sterile connector having an initially closed sterile aperture in sterile communication with the interior of the dispenser; said package sterile connector and said dispenser sterile connector being in mating engagement with each other.

U.S. Pat. No. 4,242,310, issued to Greff et al. on Dec. 30, 1980, discloses a sterile connection apparatus for enabling the connection of a first tube to a transfer tube of a medical solution container. The apparatus comprises a housing including a base portion and a cover portion adapted for interfitting with each other to provide a substantially closed interior volume. The housing includes means for receiving the first tube and means for receiving the transfer tube from a medical solution container. The housing carries means which are located within the housing and operable from outside the housing for enabling manipulation of one of the tubes with respect to the other tube. Means are provided for sterilizing the tube portions within the substantially closed interior volume.

"An Aseptic Fluid Transfer System for Blood and Blood Components", B. A. Myhre et al., Transfusion, Vol. 18, No. 5, pp. 546–552, September–October 1978, discloses a process for heat sealing two aseptic fluid transfer system (AFTS) units together. The AFTS units contain a layer of Kapton ® film (an aromatic polyimide resin which is stable at relatively high temperatures). A pair of dies, one of which is flat and one of which has a raised "H" shaped area, are brought together under a pressure of 100 psi ($6.9 \times 10^6$ dynes per square centimeter) with the AFTS units disposed between the dies. The temperature of the dies is raised to 200° C. (392° F.) over a period of 45 seconds. The dies are withdrawn and upon removal of the AFTS units from the dies, the AFTS units are heat sealed together by a seal surrounding an opening between the AFTS units. Blood bags constructed with an AFTS unit attached can thereby be joined. This system is slow and requires specially constructed units that can only be used once.

German OS No. 2,250,130 discloses a process and apparatus for bonding plastic parts by welding. The process is characterized in that the two plastic parts to be bonded to each other are pressed to a heating element introduced between the two parts; the areas of the plastic parts adjoining the heating element are surface melted by a very short and a very high temperature effect; and then, while maintaining the pressure exerted on the plastic parts, the heating element is withdrawn from the plastic parts and the two parts are immediately pressed together. The German publication does not mention plastic tubing nor how to make a sterile connection between two closed-end tubes.

U.S. Pat. No. 4,369,779, issued to Spencer on Jan. 25, 1983, discloses a process, apparatus and system for sterilely connecting two sterile, closed end tubes. The process comprises urging a hot cutting means through each tube and simultaneously forming a continuous molten seal between a heated cutting surface and a transverse section of each said tube thereby maintaining a seal between the interior and exterior of the tubes, aligning the tubes with each other and joining the respective molten ends of the tubes together to form a joint between the tubes, both while maintaining said seal.

This patent discloses an apparatus comprising a cutting means, means adapted to heat said cutting means, a pair of mounting blocks adapted to receive and hold two tubes to be joined, means to provide movement between said blocks and said cutting means to a position such that the cutting means is between said blocks and traversing where the blocks are adapted to receive tubes, means adapted to realign said blocks to a position where two different tube ends are aligned with and facing each other, and means to separate said blocks and the cutting means while urging the blocks together. The patent teaches that during the connection operation there should be no significant visible deformation of the tubes and that, in order to obtain a secure dock, the tubes to be joined must not contain more liquid than a thin film on the walls at or near the locations where they are to be cut and joined.

When using the process of this patent, it is necessary to express liquid from the tubes prior to sterile connection or at least to effect sterile connection at a portion of the tubing having an air gap of 13–25 mm (0.5 to 1 inch). There is a need for a sterile docking process which would provide sterile connection of liquid filled tubes thereby effecting a strong joint without introducing contamination or decomposition of the liquid. This is particularly true where a suitable air gap does not exist or is not desirable. There is also a need for such a process which provides total containment of the fluid within the tubes.

SUMMARY OF THE INVENTION

The present invention provides a process, apparatus, and system for sterilely connecting sterile, closed end tubes. The process comprises flattening a section of each tube to urge inside walls of each tube into contact, urging a hot cutting means through the flattened section of each tube thereby temporarily sealing together the inside walls of each tube and providing molten tube ends, aligning the tubes to be connected with each other, joining the desired molten ends of said tubes together to form a joint between said tubes, and cooling said joint and then subjecting it to stress to open the temporary seal in each tube, thereby providing fluid communication between the joined tubes. The process is broadly applicable but when used with liquid-filled tubes provides an improvement over the process of U.S. Pat. No. 4,369,779.

The apparatus of the invention comprises a cutting means, means adapted to heat said cutting means, a pair of mounting blocks adapted to receive, hold and flatten the tubes to be joined, means to provide movement between said blocks and said cutting means to a position such that the cutting means is between said blocks and traversing where the blocks are adapted to hold tubes, means for realigning the blocks to a position where two different tube ends are aligned with and facing each other, means to separate said blocks and said cutting means, and means for urging the mounting blocks together.

BRIEF DESCRIPTION OF THE DRAWINGS

FIG. 6 is a perspective view of the mounting blocks, slidably mounted on their guides and cutting means with block heater.

FIG. 7 is a perspective view of the mounting blocks fixedly arranged in a housing.

FIG. 8 is a perspective view of the welded tubes still having the temporary seals and FIG. 9 is a perspective view of the welded tubes with the temporary seals broken.

FIGS. 5–7 pertain to one embodiment of the invention.

FIG. 15 is a perspective view of the apparatus of FIG. 14.

FIG. 16 is a perspective view showing details of arms 126 and 129.

FIG. 17 is a plan view of arm 126 with the two tubes being cut by the hot cutting means.

FIG. 18 is a plan view of a portion of block 137.

FIGS. 23 and 24 are sectional views of a reweldable connector for a silastic catheter.

DETAILED DESCRIPTION OF THE INVENTION

In the present invention the tubes to be joined are flattened in an appropriate section so that the inside walls meet. Then the tubes are sequentially or simultaneously melted through by a hot cutting means with molten polymer temporarily sealing the resulting molten tube ends. Since the tubes are temporarily sealed viable airborne or surface bacteria are unable to find their way inside either of the tubes. The tubes are moved into alignment before or after the heated cutting means is slid away and then the molten tube ends are pushed together to form a joint. The joint is briefly cooled and then subjected to slight stress to open the temporary seal in each tube. The joint is sound and strong and a number of additional joints can be made in subsequent sterile connections with the same tube. Furthermore, each subsequent connection can be made at exactly the same point on the tube. The process can be used to make more than one joint at a time by using multiple (more than two) tubes and multiple tube slots.

The steps of flattening the tubes and then providing temporarily sealed tube ends are not taught by U.S. Pat. No. 4,369,779. The present process does not require the maintenance of a continuous molten seal between the heated cutting surface and a transverse section of each tube. The tubes to be connected in the process of the invention have closed ends, i.e., the tubes have sealed ends, the tube is connected to a container such as a blood bag or dialysis bag, the tube is connected to a catheter implanted in a patient, or in some other manner the tube ends are closed to the external environment. The present process will work with opened-end tubes but offers no advantage.

Figure 1:
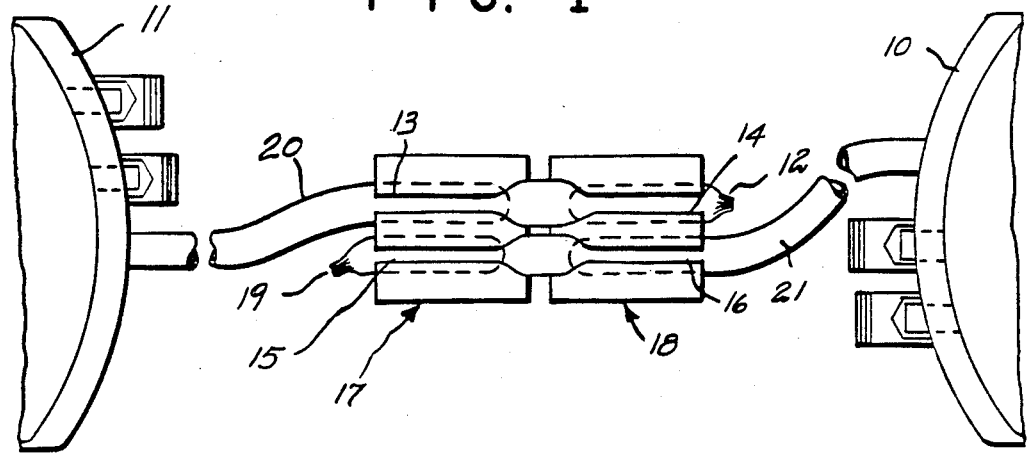
FIG. 1 is a plan view of mounting blocks used to hold two tubes which are to be joined in the starting position.

Referring now to FIG. 1, the sealed end 12 of thermoplastic tube 20 is inserted in partial slots 13 and 14, machined in blocks 17 and 18. The sealed end 19 of tube 21 is inserted in partial slots 15 and 16, machined in blocks 17 and 18. Partial slots 13–14 and 15–16 extend in FIG. 1 the length of blocks 17 and 18, respectively, except for about 1/16 of an inch at the inner facing edges and are aligned to receive straight tubing ends. The partial slots diminish in depth as the inner edge of each block is approached. The upper portions of blocks 17 and 18 have not been shown for clarity. The tubes are shown in the flattened state which results when the two portions of each mounting block are closed. In FIGS. 1-4, tubes 20 and 21 are connected to blood bags 10 and 11. Alternately, one of said tubes may be connected to a dialysis bag and the other to the patient's peritoneal cavity. Also, the tube which is connected to the patient's peritoneal cavity may be connected at the other end to a bag in lieu of having a sealed end.

Figure 2:
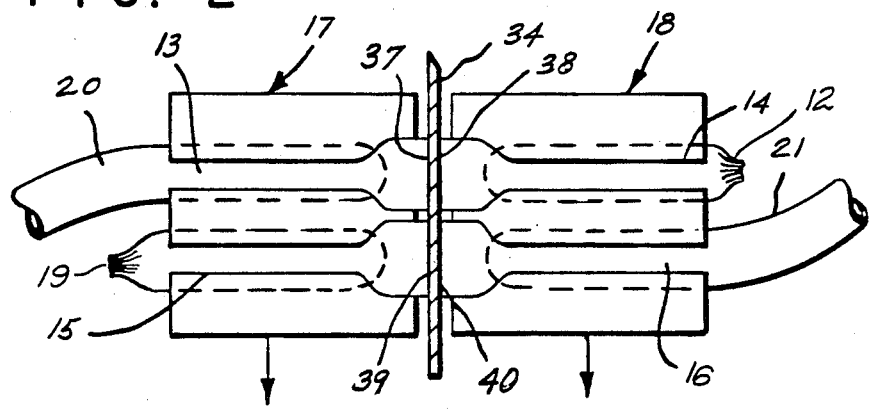
FIG. 2 is a plan view of the two tubes being severed by a hot cutting means.

Referring now to FIG. 2 the two blocks 17 and 18 have been slid in the direction shown by the arrows, relative to hot cutting means 34, which in the figure is a blade of steel, so that the cutting means has melted through tubes 20 and 21 and there are now molten temporary seals 37-38 and 39-40 sealing shut the separated portions of tubes 20 and 21, respectively. Seals 37-38 and 39-40 are created by the melting together of the inner walls of tubes 20 and 21 in the vicinity of hot cutting means 34. These molten temporary seals 37, 38, 39 and 40 prevent exchange of air between the interior of tubes 20 and 21 and the immediate outside environment of the tubes as well as contamination from particles suspended in the air or on the tubing or apparatus surface.

Figure 3:
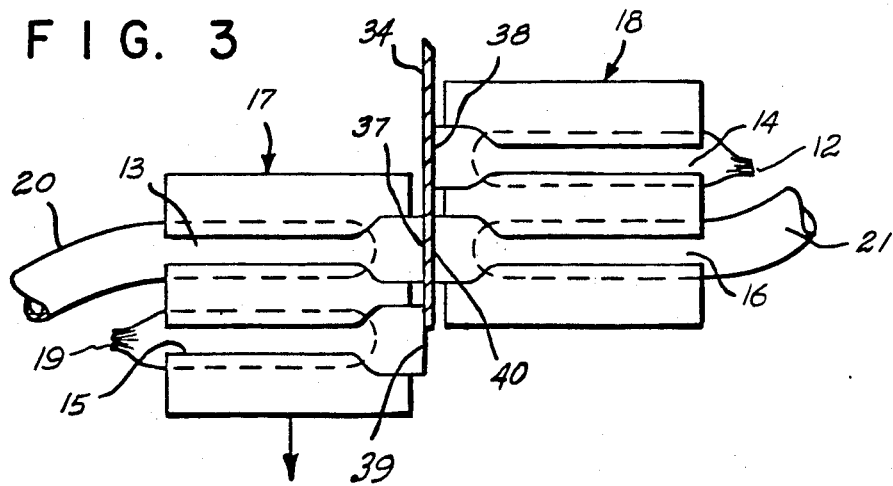
FIG. 3 is a plan view of the two tubes being repositioned and aligned opposite each other.

Referring now to FIG. 3, block 17 has been moved relative to block 18 so that partial slots 13 and 16 along with tubes 20 and 21 are aligned on opposite sides of the hot cutting means.

Figure 4:
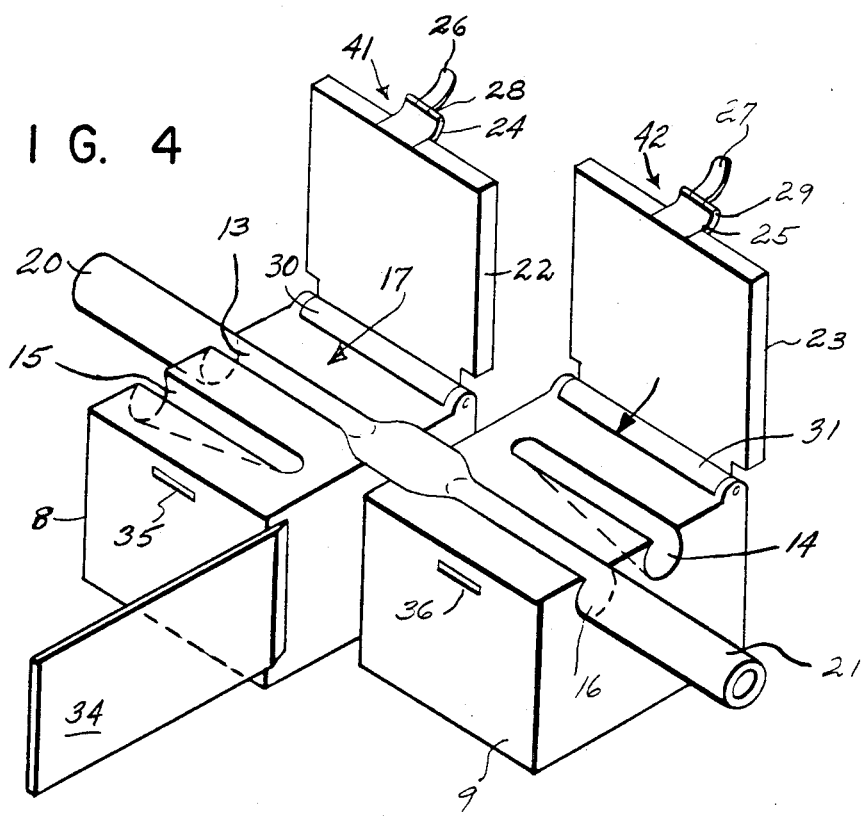
FIG. 4 is a perspective of the mounting blocks, cutting means and welded tubes.

Referring now to FIG. 4, blocks 17 and 18, with slots 13 and 16 and tubes 20 and 21 still aligned, and hot cutting means 34 have been moved relative to each other. The tube ends to be joined have been urged together and the molten tube ends have fused and thereby joined tubes 20 and 21 together. The blocks 17 and 18 holding tubes 20 and 21 were urged together by a spring 52 (shown in FIG. 5) during the time when they and cutting means 34 were being moved relative to each other. FIG. 4 also shows upper portions or lids 22 and 23 of mounting blocks 17 and 18. Lids 22 and 23 have flat inner surfaces which flatten the tubing when the lids are closed. Lids 22 and 23 are equipped with handles 41 and 42 which are securely attached by suitable means (not shown) such as soldering or by screws. Handles 41 and 42 are comprised of brackets 24 and 25 to which are attached latches 26 and 27 by hinges 28 and 29. When the lids are closed latches 26 and 27 are inserted into latch slots 35 and 36 on blocks 17 and 18 to provide pressure sufficient to flatten tubes 20 and 21 in the area of the blocks. Lids 22 and 23 are attached to the bottom portions 8 and 9 of blocks 17 and 18 via hinges 30 and 31.

Figure 5:
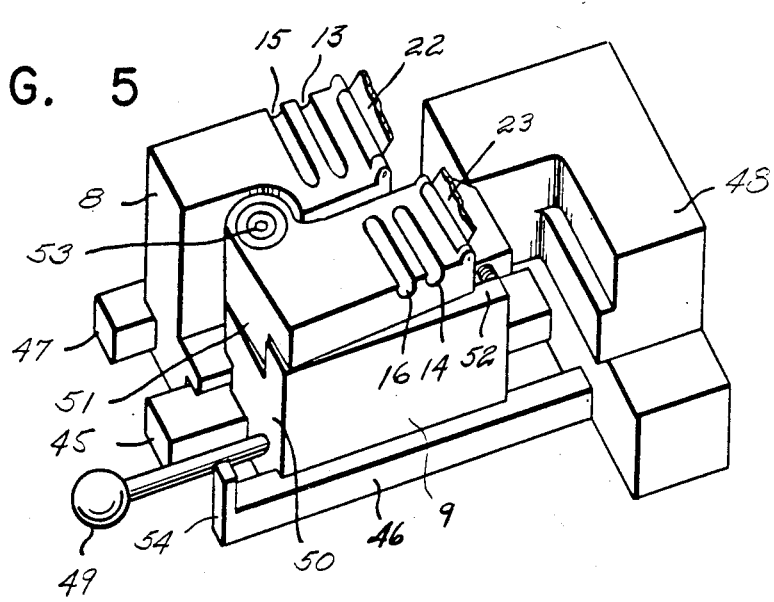
FIG. 5 is a perspective view of the mounting blocks slidably mounted on their guides.

FIG. 5 shows blocks 17 and 18 with slots 13 and 16 aligned and the blocks in the position they occupy after the weld has been made and the welded tubes have been removed. The apparatus of the invention operates similarly to the sterile docking device disclosed in U.S. Pat. No. 4,369,779 except as herein otherwise described. Hence, relevant passages of that patent are incorporated herein by reference. The blocks are shown slidably mounted on guides 45, 46 and 47. The bottom portion 9 of block 18 is composed of two parts 50 and 51 which are connected together by bolt 53 so as to allow rotational motion of part 51. Thereby, part 51 can be individually urged by spring 52 toward block 17 as the blocks and tubes (not shown) held thereby are withdrawn from the cutting means (not shown for clarity).

FIG. 5 also shows operating handle 49 and stopblock 48 against which mounting blocks 17 and 18 are pushed. Operation of this embodiment is best described by using FIGS. 5-7 along with reference to FIGS. 1-3 already described. The operator inserts tube ends in slots 13-14 and 15-16 as shown in FIG. 1. Lids 22 and 23 are closed and latched, thereby causing the tubing to become flattened in the vicinity of the mounting blocks. Cutting means 34 and block heater 55 shown in FIG. 6 are lowered so that cutting means 34 is positioned between stop-block 48 and mounting blocks 17 and 18 in alignment with the space between said mounting blocks. This positioning is effected by having block heater 55 and cutting means 34 fixedly arranged in the upper portion 57 of housing 56 shown in FIG. 7 and the mounting blocks, stop-block 48 and the accompanying slides fixedly arranged in a base portion 58 of housing 56 so that when the housing is closed the cutting means is properly situated. The two sections of the housing are attached by hinge 59.

Blade block heater 55 (FIG. 6) for heating the cutting means is activated. Blocks 17 and 18 fit together and mutually cooperate as described in U.S. Pat. No. 4,369,779. The operator pushes handle 49 which moves blocks 17 and 18 together on slides 45, 46 and 47, thereby moving the flattened tubes across hot cutting means 34 as shown in FIG. 2 and temporarily sealing the freshly molten ends of each tube. Block 17 strikes stop-block 48 first thereby causing the two blocks to become sufficiently disengaged so that block 18 moves on to stop against stop-block 48. This further movement by block 18 aligns slots 13 and 16 as shown in FIG. 3. The operator immediately withdraws handle 49 to move block 18 which is connected to the handle 49 and, by friction between the blocks, block 17 also. The blocks and the tube ends to be joined move back away from hot cutting means 34. As the corner of block 18 leaves the edge of block 48, spring 52 urges part 51 of block 18 to rotate slightly about bolt 53 toward block 17 so that a slight force is exerted on the temporarily sealed tube ends being joined as they slide off the edge of the hot cutting means (see FIG. 5). Stop 54 on slide 46 completes the motion of blocks and handle. The operator removes the joined tube after about 5 seconds delay for the joint to cool.

FIG. 8 shows tubes 20 and 21 joined at now fused temporary seals 37' and 40' to form a joint. In FIG. 9 the joint has been compressed to break the temporary seals and to provide fluid communication between the tubes.

Suitable cutting means for use in the present invention include any of the forms described in U.S. Pat. No. 4,369,779. The cutting means can also be a hot wire or a hot fluid stream as described in copending U.S. patent application Ser. No. 395,794, the pertinent disclosure of which is incorporated herein by reference. If a hot wire is employed it can be heated by electrical resistance. The wire should have sufficient strength, stiffness and chemical inertness.

Preferably, the cutting means is a heating element comprising, as an outside layer, a folded sheet of a metal having a thermal conductivity of at least about 173 watts/m°K. at a 0.10 mm thickness and a tensile yield strength of at least about $34 \times 10^4$ kPa at a 0.10 mm thickness, a resistor disposed inside the fold of said folded sheet of metal; and a layer of dielectric adhesive, stable to about 260° C., between inner surfaces of said folded sheet of metal and surfaces of said resistor, thereby bonding the resulting structure together. This heating element is described and claimed in copending U.S. patent application Ser. No. 408,417 of Benin et al., commonly assigned. In this embodiment the metal is preferably copper, the heating element is preferably an etched foil resistor made of stainless steel and the adhesive is preferably an acrylic adhesive. When the heating element or cutting means is of any of the forms described in the U.S. Pat. No. 4,369,779, it can have a thickness within the range set forth in that patent but preferably is from about 0.25 mm to about 0.36 mm in thickness.

Currently-used blood and dialysis bags and tubes are made of plasticized polyvinyl chloride for flexibility, strength and steam sterilizing. Generally, for these plasticized polyvinyl chloride tubes, the cutting means will be heated to a temperature of from about 500° F. (260° C.) to 750° F. (399° C.) which is also suitable for most other thermoplastic tubing. The preferred cutting means, copper laminated elements, will generally be heated no higher than about 600° F. (316° C.). The cutting means preferably is at a temperature high enough (1) to kill rapidly (less than one second) any bacteria or bacterial spores on the outside surface of the tubes and (2) to melt rapidly the thermoplastic resin from which the tubes are formed. The tubes are heat-sealed closed at their ends or connected to a bag. The tubes and whatever bag or bags they are connected to will have been sterilized. Below about 425° F. (218° C.) bacteria and bacterial spores are not rapidly killed by the heat from the cutting means. This temperature for rapid killing depends upon the rapidity of heat transfer from the cutting means. For example, for a solid metal blade a minimum temperature of 500° F. (260° C.) should be observed. Above about 750° F. (399° C.) most polymers such as plasticized polyvinyl chloride or polyolefins such as polypropylene or polyethylene begin to become too liquid to maintain a seal. About 520° F. (271° C.) is the preferred temperature for use with conventional plasticized polyvinyl chloride blood bag tubing when using the preferred cutting means. Another upper limit is the temperature where the resin from which the tube is made begins to degrade in the time it is exposed to the heated cutting means (about 2 seconds). For plasticized polyvinyl chloride and polyolefins the upper limit is about 300° F. (149° C.) above the melting point of the thermoplastic resin from which the tube is made.

The tube should be advanced into the cutting means at a rate such that the polymer from which the tube is fabricated melts up against the cutting means and there should be no mechanical cutting of unmolten polymer or significant visible deformation of the tube. Excessive heating times are to be avoided in order to minimize excess melting or degradation of the polymer. For conventional 165 mil (4.2 mm) outside diameter, 10 mils (0.25 mm) thick wall plasticized polyvinyl chloride blood bag tubing, a time of 0.5 to 1.5 seconds for cutting the two tubes has been found to be most satisfactory. The time for repositioning the tubes to align them should not be so slow as to cause degraded polymer to be in the welded joint. The speed of withdrawal of the cutting means is important to minimize degradation and excess melting and 0.1 to 1 second has been found to be satisfactory. A total hot cutting means contact time of about 1-3 seconds is preferred and 1.5 seconds is most preferable. After removal of the hot cutting means, cooling of the tubes takes about 3-5 seconds and the tubes are then removed from the blocks. The new joint is temporarily sealed. The joint is then subjected to slight stress, such as squeezing it lightly, i.e. 1-2 lbs. of force, to break the temporary seals, thereby effecting fluid communication between the two tubes. Slight stress can also be effected by squeezing the joined tubes remotely of the joint if the tubes are practically filled with liquid, or by any other suitable means.

The mounting blocks are preferably made of heat conductive metal to serve as heat sinks to assist rapid cooling of the joint. The tubes are preferably urged toward each other within about 1-2 seconds after the hot cutting means is removed but can be urged together as the hot cutting means is removed. It is to be understood that since the freshly obtained tube ends are temporarily sealed, it is not necessary in the present invention to maintain molten seals of polymer between the tubes and the hot cutting means and indeed such is not possible when the cutting means is a hot wire or a hot fluid stream. For a cutting means of about 0.30 mm (12 mils) in thickness and centrally located in the space between the mounting blocks and with tubes of about 5.5 mm (215 mils) outside diameter, the spacing between the blocks should be from about 0.38 mm (15 mils) to about 4.1 mm (160 mils). Preferably, the spacing between the blocks is from about 0.76 mm (30 mils) to about 2.0 mm (80 mils).

The tubing used should be formed of a thermoplastic resin which melts at least 50° F. below the temperature at which it begins to degrade in the time exposed to heat in the process of the present invention. The tubes to be joined can be made of the same material or can be made of compatible resins. "Compatible resins" as used herein means that the melting points of the two materials are close enough so that at the operating temperature both form thick, viscous melts which will flow together to form a single melt phase without polymer degradation or formation of thermal or other chemical reaction products which would weaken or otherwise interfere with formation of the single melt phase and its subsequent cooling and solidification to a strong joint. For example, polyethylene is compatible with polyethylene copolymers and polypropylene.

In a preferred embodiment of the invention the means for providing movement between the blocks and the cutting means, the means to realign the blocks and the means to urge the blocks together are cam means for providing movement generating three orthogonal motions. The cam means preferably is a driven cam cylinder containing one groove in each face and one groove around its periphery. One of the mounting blocks is coupled to the groove in one face of the cam and to the groove around the periphery of the cam. The cutting means is coupled to the groove in the other face of the cam.

In this embodiment the apparatus preferably has a controller coupled to the cam cylinder to control the timing of the operation of the apparatus. In this embodiment of the invention the apparatus is similar to the automatic sterile connection device disclosed in U.S. patent application Ser. No. 408,418, filed on Aug. 16, 1982 and commonly assigned. It is to be understood that the apparatus of the invention differs from the apparatus of said application in those aspects which are necessary to effect the spirit of the present invention.

Figure 10:
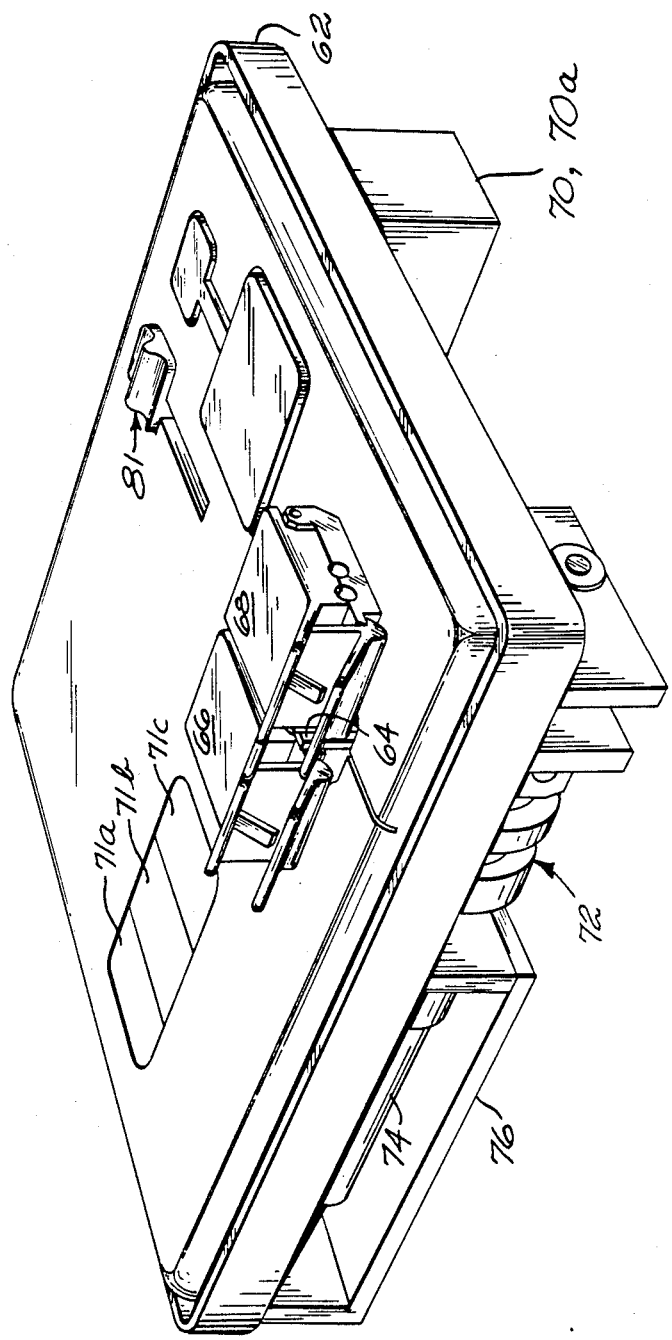
FIG. 10 is an isometric view of an automatic sterile connection device of the invention.

Referring to FIG. 10, the sterile connection device chosen for purposes of illustration of this embodiment is denoted generally as 60 and includes as major components a housing 62, a cutting mechanism 64 pivotally connected to the housing, a pair of mounting blocks 66, 68 spaced from each other in the same plane, an evacuation pump 70a driven by a motor 70, a cam cylinder 72 driven by a motor 74 and an electronic control unit 76. The cutting means is a heating element of the preferred mode previously described herein. The specific embodiment disclosed also includes push buttons 71a, 71b and 71c for checking a battery used for the cutting means, for indicating when the system is ready, and for initiating the sterile connection operation, respectively. Also shown are magazine 79 for holding fresh heating elements and load-eject lever 81 for feeding the heating elements into the cutting mechanism.

Figure 11:
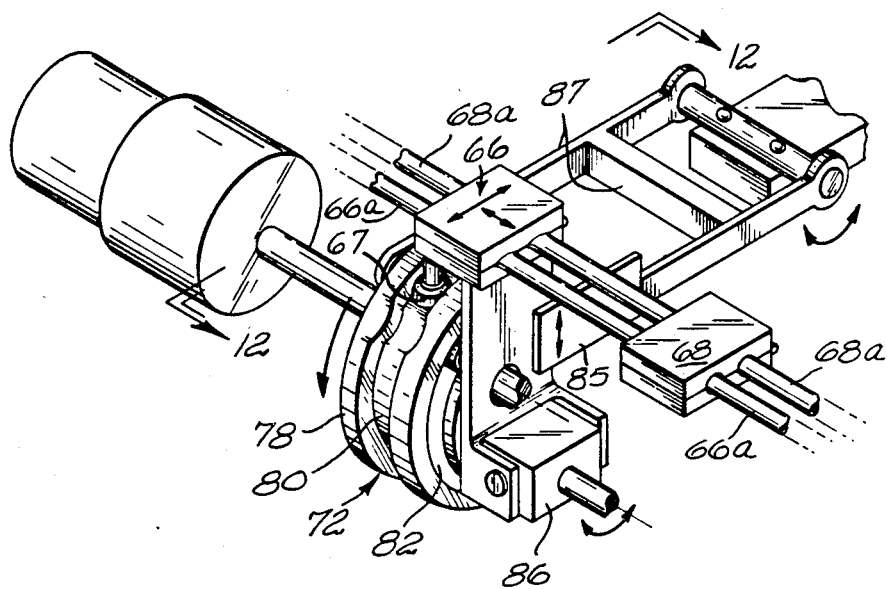
FIG. 11 is an isometric view partially broken away of the driven cam used to move the mounting blocks and the cutting means of the sterile connection device of FIG. 10.

The mechanism for generating the three orthogonal motions required for splicing is seen in FIG. 11 which shows a typical arrangement of that mechanism. More particularly, it involves three cams to accomplish the three motions. In the preferred embodiment shown, the cams are grooves 78, 80, 82 on different faces of cam cylinder 72. This arrangement ensures that the three cams never get out of phase. A heating element holder 87 for heating element 85 is pivotally attached to housing 62 at one end and is engaged in cam groove 78 at its other end. The heating element 85 is positioned between mounting blocks 66, 68 and below the tubes 66a and 68a held side-by-side in the blocks for splicing. A pivoting block 86 is journaled in housing 62 at one end and journaled to mounting block 66 at its other end. Mounting block 66 intermediate to its ends is engaged in cam groove 82. Mounting block 66 is also engaged in peripheral cam groove 80 via follower 67 while mounting block 60 is fixed to housing 62. Motor 74 rotates cam cylinder 72.

The heating element 85 is an etched stainless steel foil resistor laminated between sheets of copper connected to a battery. In use, it is subjected to a short heating cycle (about 6 seconds) and to one-shot use (a new heating element is used for each splice).

The sterile connection operation with the apparatus disclosed utilizes three orthogonal motions involving mounting block 66 and the heating element 85. These are lifting the heating element 85 through the tubes 66a and 68a, shifting the tubes to align the ones to be joined together and finally urging the tubes together while or after withdrawing the heating element. In the specific embodiment shown the tubes are urged together while the heating element is withdrawn. The cam cylinder 72 commences rotation (FIG. 12) in the direction of the arrow and with this rotation cam groove 78 lifts heating element 85 upwardly through the tubes 66a, 68a. With the heating element 85 dwelling between the tubes, continued rotation of the cam cylinder causes cam groove 82 to move mounting block 66 aligning the tubes 66a, 68a. Continued rotation of the cam cylinder causes peripheral cam groove 80 to urge mounting block 66 toward fixed mounting block 68 as heating element 85 is lowered. Thus tubes 66a, 68a which are each temporarily sealed are pushed together forming a sterile connection between them. The tubes are removed from the blocks and squeezed to break the temporary seals, thereby effecting fluid communication between the two tubes.

Figure 13:
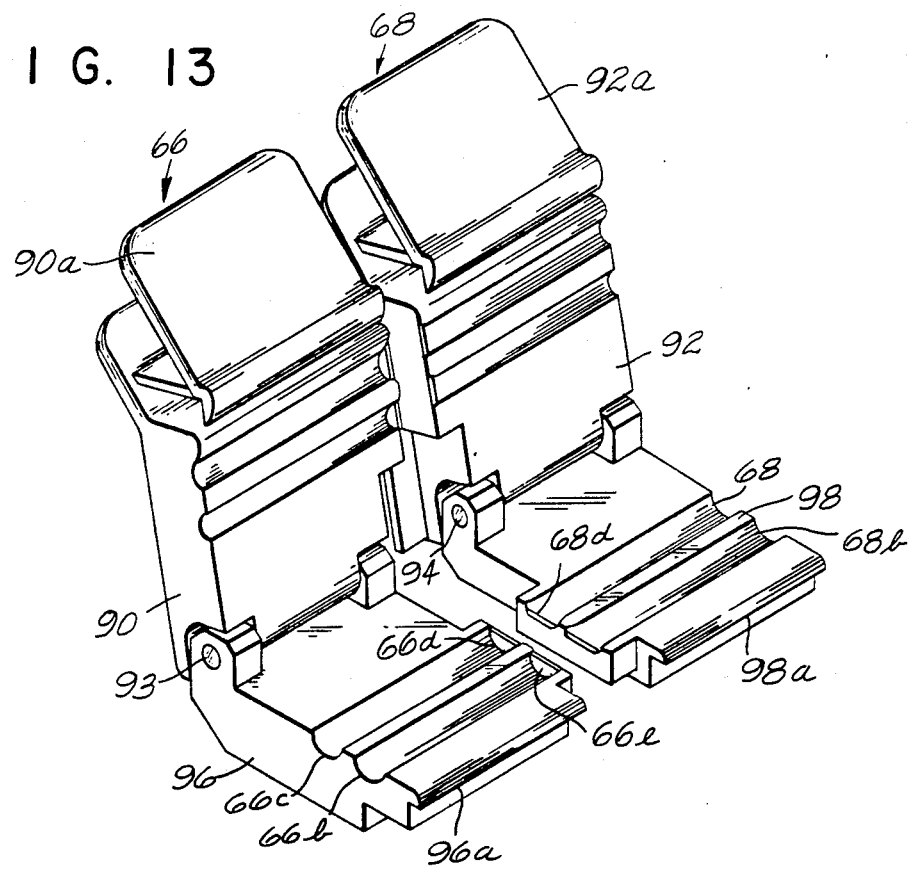
FIG. 13 is an isometric view of the mounting blocks used in the apparatus of FIG. 10.

As best shown in FIG. 13, the tube mounting blocks 66, 68 include covers 90, 92 pivotally attached at hinge points 93, 94 to tube holder bases 96, 98. Full channels 66b, 66c are provided in mounting block 66 to hold the tubes to be spliced and mounting block 68 is similarly equipped with full channels 68b, 68c. The channels flare out at their facing ends and have raised lips 66d, 66e, and 68d, 68e for flattening the tubes. Inside surfaces of covers 90, 92 are similarly configured. When the covers 90, 92 are closed latches 90a, 92a are placed over lips 96a and 98a of the respective bases 96 and 98 to create sufficient force to flatten the tubing.

The operation of the heating element load and ejection system and the controller are not essential elements to the present invention. Suitable systems and their operation are described in U.S. patent application Ser. No. 408,418, the pertinent passages of which are incorporated herein by reference.

Figure 14A:
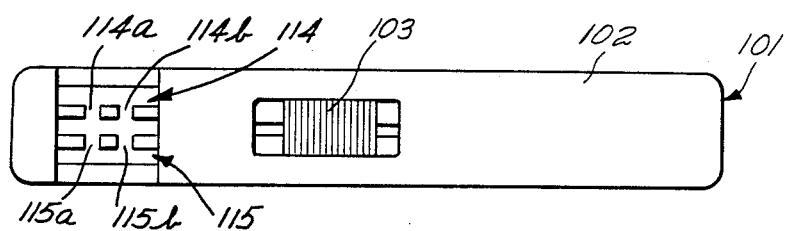
FIGS. 14a and b are plan and side views of another embodiment of the apparatus of the invention.

FIGS. 14a and b illustrate another embodiment of the apparatus of the invention. In this embodiment the device has a wand shape and is hand held, thereby enabling it to be used in places which are accessible with difficulty. The device chosen for purposes of illustration is denoted generally as 101 and includes as external components housing 102, a pair of mounting blocks 114 and 115 providing tube slots 114a, 114b and 115a, 115b, respectively, cover 104 and switch 103.

Referring to FIG. 15 mounting blocks 114 and 115 comprise outer walls 114c and 115c having U-shaped tube slots 114a, 114b and 115a, 115b. The front walls 111 and 112 of the mounting blocks are linearly movable as are the rear walls 116 and 117. Connected to rear walls 116 and 117 are linkages 118 and 119, respectively, which provide for flattening of the tubes as will be later explained. The front and rear walls of each mounting block are integral with the front and rear portions of the inner walls. The middle portions 113a and 113b of the inner walls are fixedly attached to the bases 138 and 139, respectively. The base and outer wall of each mounting block is an integral portion of block 133, 134 which extends into sleeve 135. Sleeve 135 is shown with top portion cut-away to further illustrate additional elements. In practice, this sleeve would extend to cover linkages 118 and 119. Cutting means 141 is aligned below the space in the mounting blocks and rests rigidly but removably in holder 140 which is fixedly attached to arm 126.

Figure 14B:
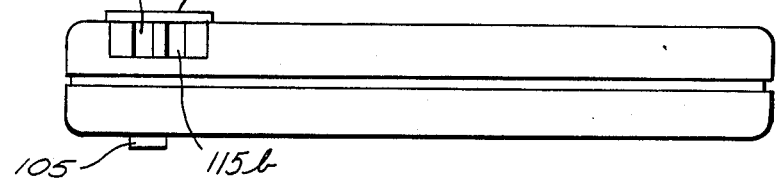

Arm 126 extends rearwardly and has an upwardly raised portion (see FIG. 16) which extends into sleeve 135. Arm 126 contains cam surface 125 which rides on pin 127 providing lift action for the cutting means holder 140. Pin 127 is fixedly attached to actuator tab 128 which in turn is fixedly attached to block 123. Block 123 is fixedly attached to ball reverser bushing 107 which rides on ball reverser shaft 124. DC motor 122 imparts rotational motion to ball reverser shaft 124 when activated. Arm 126 pivots about pin 145 which is fixedly attached to arm 129. Another pin (not shown) attached to the other side of actuator tab 128 extends through slot 147 in arm 129. When this pin has moved to the extreme right it serves to move arm 129 under the tubes after they have been connected. When rod 105 (FIG. 14b) is pushed it lifts arm 129 up against the freshly joined tubing to apply sufficient force to open the joint. Motor 122 and sleeve 135 are fixedly attached to housing 102.

Operation of embodiment is best understood by referring to FIGS. 14a and b FIG. 18. The operator places the two tubes to be joined in the slots in mounting blocks 114 and 115. He then pushes switch 103 forward causing the bottom of the switch to move across the top of linkages 118, 119 thereby flattening them. Flattening of the linkages causes the front walls 111 and 112 and rear walls 116 and 117 of the mounting blocks to move together toward stationary portions 113a and 113b thereby flattening the tubes. The forward motion of this switch also serves to close lid 104 and to activate current to motor 122 and cutting means 141 through a conventional system of wires and contacts (not shown). Block 123 moves forward carrying with it actuator tab 128. As actuator tab 128 moves forward, arm 126 is raised so that hot cutting means 141 traverses tubes 153, 154 and melts through them (see FIG. 17). Projection 155 extends into slot 156 in block 137 and engages wedge 157 just after the cutting means has melted through the tubes whereby mounting block 114 is moved forward to align opening 114b with 115a and thus the tube portions contained therein. Forward motion of mounting block 114 is terminated by a stop (not shown) fixedly attached to housing 102. Forward motion of the cutting means terminates when projection 130 reaches the end of slot 131.

Arm 126 continues its forward travel causing cutting means 141 to move beyond the tubes. As or after the blade has passed the two tubes to be connected, portion 136 of mounting block 115 is pivoted about pin 149, which is fitted in bracket 151, through the action of a spring (not shown) to cause the portion of block 115 in front of section 152 to be urged toward block 114 thereby joining the two tubes. The operator allows the joint to cool and then pushes rod 105 (FIG. 14b) to cause arm 129 to elevate and press the joint open providing fluid communication between the tubes.

The working elements comprising this embodiment can be used in the wand model illustrated or can be used in devices of the invention resembling a hand-held calculator or a gun. Each of these configurations provides features more amenable to certain environments. For instance, the gun model would be more adaptable to one-hand operation.

The tubing flattened in the mounting blocks can have a small portion, occupying the space between the mounting blocks, wherein liquid can be trapped. In the present invention the tubes can be flattened (1) only enough that at the edges of the tubes the inside walls are not in intimate sealing contact or (2) so that the inside walls are in complete intimate sealing contact. In the first mode, residual liquid in the tubing occupying the space between the mounting blocks flows past the flattened area into the round portion of the tubing during passage of the hot cutting means. Hence, any liquid in the tubes is retained therein and a strong, occlusion-free joint results; however, the stub ends of the tubes may not be sealed fluid-tight.

The second mode can be effected in any of several ways, results in the stub ends of the tubes being sealed fluid-tight and thereby provides total containment. In one embodiment, prior to being flattened with the mounting blocks, the two tubes are flattened with a clamp in the space between the mounting blocks. In this embodiment all fluid is displaced from the portion of the tubes involved in the sterile connection operation. Employment of a clamp would also be useful in situations where the tubing is very stiff. Alternatively, the mounting blocks can be spaced apart a distance which maintains the tubing flat in this section thereby preventing the trapping of liquid. For instance, with tubes of about 5.5 mm (215 mils) outside diameter, the spacing between the blocks should be from about 0.38 mm (15 mils) to about 1.0 mm (40 mils), preferably about 0.76 mm (30 mils). In either mode of operation, the hot cutting means can be withdrawn prior to alignment of the tubes. The tubes can then be aligned and joined to give a sterile joint provided that they are not allowed to cool significantly before joining.

Figure 19:
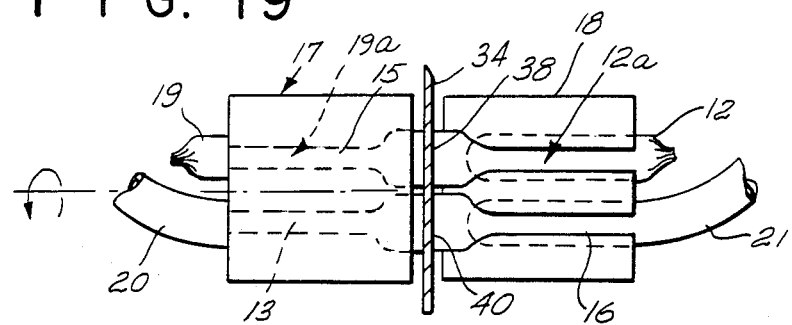
FIG. 19 is a plan view of the mounting blocks with the left block rotated 180°.

In this total containment mode as described thusfar herein, the freshly molten tube ends which are not connected to make a joint emerge with temporary seals which can be made permanent by use of a Hematron ® device. Referring to FIGS. 2 and 3, one can see that, when tubes 20 and 21 are melted through by hot cutting element 34 and shifted into alignment, sealed end 12 of tube 20 and sealed end 19 of tube 21 will have temporary seals on the ends adjacent to cutting element 34. Use of a Hematron ® device can be avoided and permanent seals can be effected by either of two other features of the present invention. FIG. 19 illustrates one alternative to the alignment depicted in FIG. 3. In this embodiment, one of the mounting blocks is rotated 180° about the central horizontal axis parallel to the axis running through the center of each flattened tube. This rotation brings tubes 20 and 21 and stub ends 12a and 19a, respectively, into alignment. After the hot cutting means 34 is withdrawn, tubes 20 and 21 are urged together and stub ends 12a and 19a are at the same time urged together to form joints. Each cooled joint can be compressed slightly to provide fluid communication between the joined sections of tubing.

Figure 20:
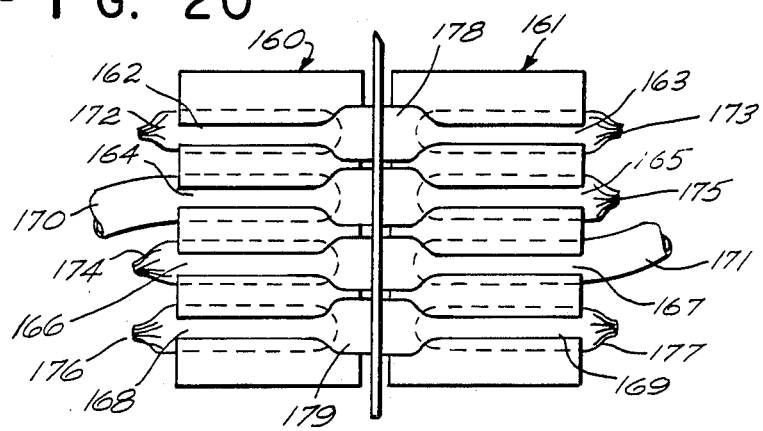
FIGS. 20 and 21 are plan views of mounting blocks with four slots each.
Figure 21:
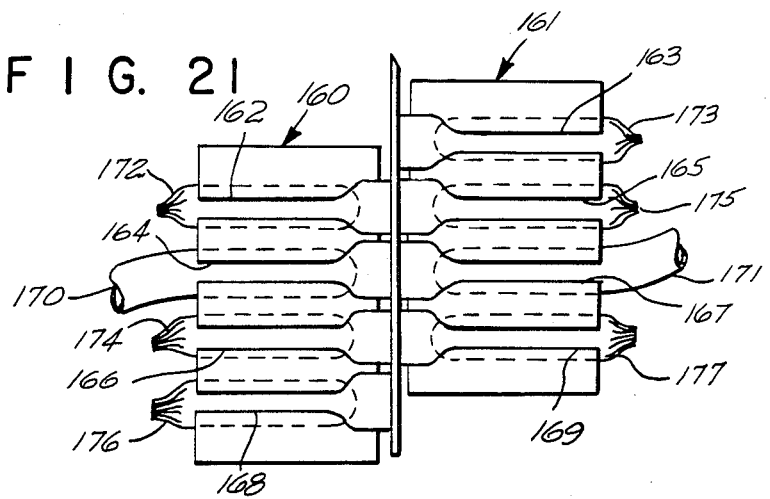

A second alternative to use of a Hematron ® device for obtaining permanent seals in the total containment mode is illustrated by FIGS. 20 and 21. FIG. 20 shows mounting blocks 160 and 161 having, respectively, partial slots 162, 164, 166 and 168 and 163, 165, 167 and 169 machined therein. Other than there being four slots in each block, the slots are similar to those illustrated in FIGS. 1-4. Sealed end 175 of tubing 170 is inserted in slots 164 and 165. Sealed end 174 of tubing 171 is inserted in slots 166 and 167. Short pieces of tubing 178 and 179, each having both ends sealed (162, 163 and 176, 177, respectively) are inserted in slots 162, 163 and 168, 169. The hot cutting means is urged through the four pieces of tubing; the tubing is aligned so that the desired sections are facing each other (FIG. 21); the cutting means is removed; and the molten ends are urged together. This operation results in tube end 174 of tubing 171 and tube end 175 of tubing 170 being joined to sealed tube end 177 and sealed tube end 162, respectively, to provide permanent sealing of ends 174 and 175. When employing either of these alternative modes, preferably a cam operated unit is utilized.

A "seal" is the closure of a tube end; "connection" means the welded joint which holds two tubes together; and "temporary" means that a seal can be opened with light force, i.e., 1–2 lbs if the operator so desires but otherwise the seal remains shut. A "temporary seal" may have pinholes. "Fluidtight temporary seal" means a closure which does not have pinholes and does not permit ingress or egress of fluid. "Stub ends" are the tube ends which are not to be joined. Between a spacing of about 1.0 mm (40 mils) and about 2.0 mm (80 mils), preferably about 1.5 mm (60 mils), temporary seals which are fully closed, i.e., no pin holes, can be obtained after the cutting means is withdrawn. However, some egress of fluid may occur prior to withdrawal.

The apparatus of the invention can form part of a sterile connection system for continuous ambulatory peritoneal dialysis in which a dialysis solution container with a transfer port that includes a segment of tubing is coupled to a tube extending from an implanted catheter opening into a patient's peritoneal cavity. In this embodiment of the invention the patient's tube and/or the transfer tube can have an entry port with a protective cover or a sealed distal end but preferably both have a sealed distal end. This system minimizes the possibility of peritonitis and permits any other treatment bag, such as a bag of antibiotic, bacteriostat, or other medication to be connected as desired. Moreover, this embodiment offers the additional advantage of eliminating the need for the patient to carry the empty dialysis solution bag because the bag can be sterilely disconnected by using the apparatus of the invention to melt through the tube and heat seal both the patient tube and the bag tube. In this mode, a second tube is not placed in the tube slots. The freshly separated tubes are allowed to cool and then, if desired, are permanently sealed by use of a Hematron ® device. This embodiment also eliminates the need for the present laborious procedure used to achieve sterility.

In another embodiment, the apparatus of the invention forms part of a sterile connection system for connecting two blood bags. One of the bags can be a donor bag and the other a transfer bag. The donor bag will have a blood collection tube and optionally can have a transfer port with a transfer tube. The transfer bag has a transfer tube (connection tube). The two bags can be sterilely connected by joining the connection tube of the transfer bag to the transfer port of the donor bag. The transfer port of the donor bag can be a conventional entry port, e.g., having a protective covering and a septum inside the port. The bags can also be connected by joining the blood collection tube of the donor bag to the connection tube of the transfer bag.

In the preferred embodiment for both the blood bag system and the CAPD system, the donor bag and dialysis bag have, specifically for sterile connection, an additional tube (pigtail) which is connector-free and has a sealed distal end. The term "connector-free" as used herein means the tube does not bear any of the conventional fittings, such as a plastic fitting with a diaphragm, a low-melting thermoplastic insert, an insert fusable by radiant energy, or the like. The tube has a sealed distal end which is prepared solely by sealing the tube end together by use of heat, solvent or the like.

In the present system for the sterile connection of blood bags, the need to pre-assemble bags into a system is eliminated. It is to be understood that the expression "blood bag" as used herein refers collectively to either the donor (primary) bag or the satellite bag. With the present invention satellite bags can be sterilely connected to a donor bag as the need arises. The donor bag can be made from a wet-sterilizable material, such as polyvinyl chloride whereas the satellite bags do not have to be wet-sterilizable but can be made of material which can be sterilized only by dry-sterilization means, such as irradiation or ethylene oxide treatment. For example, the satellite bag can be constructed from $O_2$ permeable polyethylene which would increase platelet viability. Alternatively, the satellite bag can be made from a polyethylene copolymer, a polyethylene laminate, polypropylene, or any other material which is compatible with the material from which the donor bag is constructed. The satellite bag can be made from material which is incompatible with the material from which the donor bag is constructed so long as the tubes to be connected are made of compatible materials. For instance, the donor bag and its tubing can be made from polyvinyl chloride whereas the satellite bag can be made from polyethylene but its tubing made from polyvinyl chloride and solvent welded to the satellite bag. Techniques for solvent welding are well known in the art. Supplemental treatments can be sterilely added and washing to remove treating agents can be sterilely effected. Some practitioners believe hepatitis risks can be reduced by washing red cells without previous freezing.

The sterile connection apparatus of the invention can also be used to provide a system for producing sterile, nonautoclavable body fluid containers having wet-sterilized (autoclaved) liquid therein. The system is similar to that described in U.S. Pat. No. 4,223,675; however, the present apparatus eliminates the need to have special connectors attached to the tubing.

With the present invention a dry-sterilized package can be formed from a synthetic resin material which is unsuitable for being subjected to wet-sterilization conditions but is particularly suitable for prolonged storage of body fluids. The autoclavable liquid is placed in an autoclavable dispenser equipped with an access tube which can then be heat-sealed closed. The dispenser package and liquid are then wet-sterilized in an autoclave. The dispenser package is next sterilely connected to a dry-sterilized container by using the apparatus and process of the invention. The dry-sterilized container can be equipped with a connector-free tube having a sealed distal end, said tube being specifically for sterile connection. After the sterile connection is made the autoclaved liquid is transferred to the dry-sterilized container which is nonautoclavable. If desired, the two containers can be separated by using the apparatus of the invention to melt through and heat seal the connecting tube so that each container is left with a connector-free tube having a sealed distal end. Other packages can be connected to either container by subsequent sterile docking operations. The autoclavable liquid can be an anticoagulant and the autoclavable dispenser package can be constructed from polyvinyl chloride. The nonautoclavable container can be a blood bag constructed from materials such as those previously described herein.

The process of the invention for joining two thermoplastic tubes together transversely of the axis of each tube can be carried out using the herein-described specific embodiments of the apparatus of the invention but is not limited thereto. As used herein, transverse means crosswise the axis of each tube but not necessarily at a right angle with said axis. The tubes can be flattened in a horizontal, vertical or diagonal plane; however, a diagonal plane is preferred for convenience when employing a controller operated cam cylinder unit and copper laminated cutting element is described earlier herein.

Figure 22:
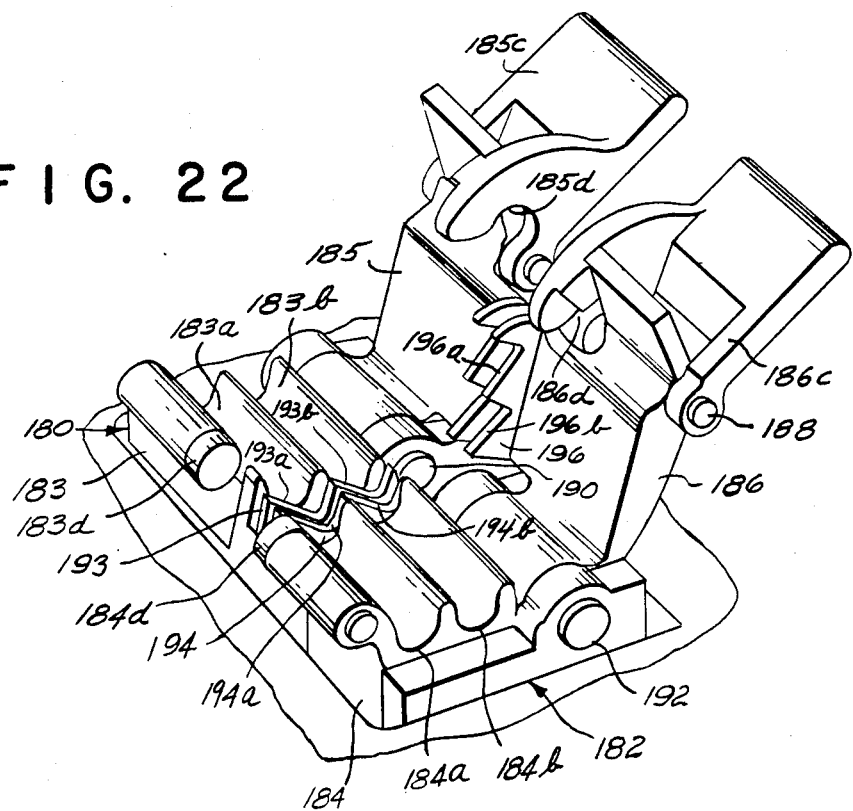
FIG. 22 is a perspective view of another embodiment of the mounting blocks.

FIG. 22 illustrates tube mounting blocks 180 and 182 designed for flattening the tubes in a diagonal plane. The tube mounting blocks 180, 182 include covers 185, 186 pivotally attached at hinge points 190, 192 to tube holder bases 183, 184. Slots 183a, 183b are provided in mounting block 180 and slots 184a, 184b are provided in mounting block 182 for holding the tubes to be spliced. At the inside facing ends of slots 183a, 183b and 184a, 184b are jaws 193 and 194, respectively. Jaw 193 has flat surfaces 193a, 193b and jaw 194 has flat surfaces 194a, 194b for flattening the tubes when the upper and lower halves of each mounting block are closed. Cover 186 of mounting block 182 has a corresponding jaw 196 with flat surfaces 196a, 196b for cooperating with flat surfaces 194a, 194b. Cover 185 is similarly equipped. The flat surfaces of the jaws are at about a 35° angle with the horizontal plane.

Inside surfaces of covers 185, 186 are flat. Covers 185, 186 have pivoting cam portions 185c, 186c, respectively, which fit over rollers 183d, 184d of bases 183, 184 when the covers are closed to create sufficient force to flatten the tubing. Pivoting cam portion 186c is held in an up-position about its pivot by friction created by a spring washer (not shown) inserted in pivot hinge 188. Pivoting cam portion 185c is similarly configured. When closing of the mounting blocks is initiated and the flattening jaws of the covers contact the tubes, covers 185, 186 no longer pivot freely so that cam portions 185c, 186c begin to pivot and engage on rollers 183d, 184d of bases 183, 184. As the pivoting cam surfaces 185d, 186d engage the rollers, they pull the cover jaws down against the tubes causing the tubes to flatten against lower jaws 193, 194. When cam portions 185c, 186c are fully pivoted, the tubes are completely flattened and the rollers fully engaged to maintain mounting blocks 180, 182 closed.

The cutting means can be urged through the flattened tubes in any transverse direction regardless of the plane in which the tubes are flattened. With the process of the invention the tube ends which result from the "melting through" step and which are not to be connected are preferably temporarily sealed fluid-tight, thereby eliminating the need to clamp them shut or to connect onto them closed, stub tube ends. Permanent seals can be subsequently obtained by use of a Hematron ® device or by a 180° rotation of one of the mounting blocks in lieu of shifting for alignment.

In the process of the invention occlusion of the interior of the joined tubes is eliminated and subsequent connections can be made at the same place on a tube. The latter feature provides another aspect of the invention. The CAPD patient has a surgically implanted silastic catheter which has an external titanium connector to which a polyvinyl chloride tube having a spike (administration set) is attached. It is necessary to replace the polyvinyl chloride tube about once per month. This replacement provides a source of potential infection of the peritoneum.

In the present invention the titanium connector can be replaced by a tube, rewreldable connector 200 (see FIG. 24), made of a thermoplastic resin, such as a polyester, polyurethane or polypropylene, which is connected to the silastic catheter 205 and the polyvinyl chloride tube 207 by suitable plastic fittings 202, 203. Replacement of the administration set can then be effected by using the process of the invention to connect a new administration set. Referring to FIG. 23, the new set prior to connection has an end 209 with a fitting connecting a sealed tube of the selected thermoplastic resin and is then sterilely connected to the portion 211 of the rewreldable connector attached to the silastic catheter. With the process of the invention the catheter when implanted can have its rewreldable connector end thermally sealed and the administration set can be connected by utilizing the present invention.

The apparatus and process of the invention are also useful in other peritoneal dialysis therapies, such as intermittent peritoneal dialysis (IPD), continuous cycled peritoneal dialysis (CCPD), and other therapies using the peritoneal membrane, can beneficially be employed in urinary drainage, and can be used in the manufacture of sterile medical supplies and in other sterile packaging processes. IPD is a machine-automated peritoneal dialysis wherein dialysate is prepared from a concentrate and then delivered to a patient with machine control of inflow and dwell time over a predetermined period of time. CCPD is a machine-automated peritoneal dialysis wherein exchanges of peritoneal fluid are performed automatically at night and the abdomen is left full during the daytime.

In conventional urinary drainage, an in-dwelling urinary catheter is placed in the bladder/urethra to relieve temporarily anatomic or physiologic urinary obstruction, to facilitate urological surgery, or to permit accurate measurement of urinary output in severely ill patients. The catheter is connected to a drain tube which is connected, in turn, to a urinary drainage bag which is typically accessed three times per day for drainage.

Urinary tract infection is a major risk associated with present urinary drainage procedures, and a strong need for sterile access exists. The device and apparatus of the present invention fulfill that need. The apparatus of the invention when used with suitable disposables can be used for sterile access for bag removal or replacement and for irrigation. The drainage system for this use consists of a Foley catheter connected to a drain tube which is connected to a low-cost disposable drainage bag, additional disposable drainage bags having a connector-free tube specifically for sterile connection and with a sealed distal end; irrigation bags and syringes similarly having a connector-free tube with a sealed distal end; and a sterile connection device. Instead of draining the bag three times per day, the used drainage bag can be sterilely disconnected and a new bag sterilely connected thrice daily. For this embodiment the apparatus of the invention would be employed in the total containment mode.

One example of other sterile packaging processes where the apparatus of the invention can be beneficially employed is in the packaging of sterile milk and fruit juices. In the current commercial production, the contents and package are sterilized separately, then combined in a sterile packaging system. The package includes a drinking straw. Difficulties have been encountered by the consumer in opening the packages and using the drinking straw incorporated therewith.

With the apparatus of the invention the container can be a polyethylene bag with an access port (tube) as the drinking straw. During the packaging operation the straw can be sterilely temporarily sealed with the apparatus of the invention. The package can be opened for drinking by application of finger pressure to force open the sterile, temporary seal.

The invention is further illustrated by the following example in which all temperatures are in degrees Celsius and all percentages are by volume unless otherwise stated.

EXAMPLE

Figure 12:
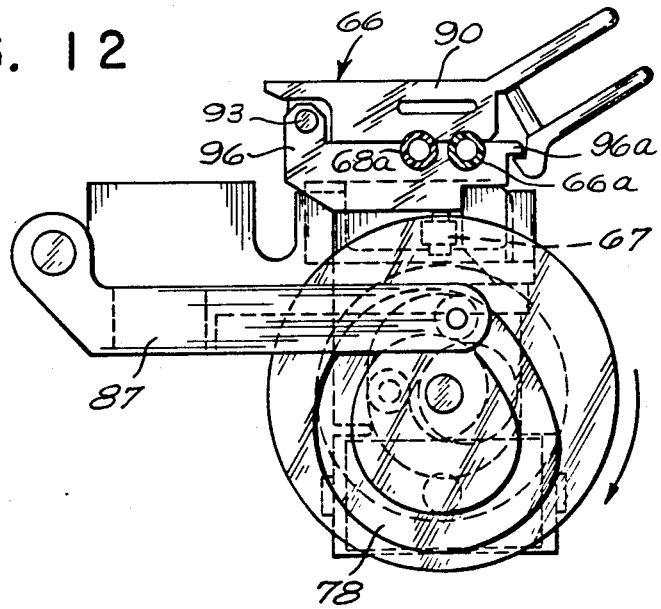
FIG. 12 is a view of FIG. 11 taken along line 12—12.

The apparatus used was a cam operated device as described herein in reference to FIGS. 10–12 and had a pair of stainless steel tube mounting blocks (FIG. 22) each about 1⅛ inch (2.86 cm) by 1.5 inch (3.81 cm) by 0.75 inch (1.9 cm) and each hinged in halves so they could be opened. In the bottom half of each mounting block there were two slots, 0.31 inch (0.79 cm) apart center to center and 0.21 inch (0.53 cm) wide and 0.21 (0.53 cm) deep, for holding the tubes to be welded. At adjacent ends of each mounting block and spaced 0.05 inch (0.13 cm) away from the slots were 0.06 inch (0.15 cm) wide jaws for flattening each tube symmetrically with respect to the round tube axis. The opposing faces of these jaws on the adjacent mounting blocks were spaced about 0.05 inch (0.13 cm) apart. The upper half of each mounting block had a matching 0.06 inch (0.15 cm) wide flattening jaw adjacent a flat surface that, when pivoted to meet the lower half, formed a covering over the open tube slots.

One mounting block was stationary while the other was pivotably moveable in two orthogonal directions. A laminated welding wafer (cutting means), 0.50 inch (1.27 cm) high and 1.35 inch (3.43 cm) long and 0.012 inch (0.03 cm) thick, was pivotably held below the tube slots with the 0.012 inch (0.03 cm) dimension centered in the 0.05 inch (0.13 cm) gap between the mounting blocks. The wafer was rigidly supported on three edges. Electrical contacts engaged the resistor contact pads exposed on one face of the wafer. The wafer was heated by a constant 1.35 amp DC source.

For each joint made, two sections of plasticized polyvinyl chloride tubing with 215 mil (5.5 mm) outside diameter and 32 mil (0.81 mm) thick walls were pressed into the slots. The mounting blocks were closed, thereby flattening each tube in the area of the jaws. The wafer was activitated. When its temperature reached about 271° (520° F.) (after about 5–8 seconds), the wafer was pivoted up about 0.4 inch (1.02 cm) to melt through both flattened tubes simultaneously while the current continued to power the wafer. The moveable block was then pivotably shifted about 0.31 inch (0.79 cm) to align the tubes to be joined. The wafer was then pivotably lowered at the same time as the moveable block was pivotably shifted about 0.35 inch (0.89 cm) toward the fixed holder to squeeze together the molted tube ends to be joined. The wafer current was turned off as it reached the lowered position. The time for the wafer to raise, the moveable block to align the ends to be joined, and the wafer to return to its lowered position while the ends were squeezed together was about 3.0 seconds. The joined tube ends were then allowed to cool for at least about 5 seconds before they were removed from the holders. The flat tube joint was then popped by manually squeezing the joint between ones fingers.

The wafer was replaced for each joint. The joined tubes had about 70% of their original strength when pulled in tension and did not leak.

Using the above-described apparatus and procedure twenty joints were made. The tubes used in the forward slots were twelve inches (30.5 cm) in length and were approximately 60% full of a nutrient solution for bacteria growth. The tubes had been closed on both ends by heat sealing with a Hematron ® device and were sterile on the inside. The outside of each tube was coated with spores of *Bacillus circulans*. Seventeen of the tubes used in the rear slots were 6 inches (15.2 cm) long, half full of nutrient solution, heat sealed at both ends and sterile on the inside. The other three tubes were twelve inches (3.05 cm) long, sixty percent full and otherwise the same. None of the tubes used in the rear slots was coated with bacteria.

For each joint the tubes were placed in the mounting blocks in the same manner. Each of the two tubes for each joint was oriented so that the end of the tube containing air was to the right (the mounting blocks were positioned similar to orientation shown in FIG. 22). The tubing was positioned so that the site of severance was approximately 3.5 inches (8.9 cm) from the right end of the rear tube and 4.5 inches (11.4 cm) from the right end of the front tube. There was a column of liquid in the path of the wafer in each tube. The left mounting block was closed first and then the right mounting block was closed. This resulted in an initial pressure inside the tubing at the weld site of about 2 psig.

After the joints were made, they were squeezed to break the temporary seals which kept the tubing flat at the weld, and thereby providing fluid communication between the two tubes for each joint. The joined tubes were then incubated at 35° for four days. All of the joined tubes so incubated showed no evidence of their interiors being contaminated by bacteria, the presence of which would have been shown by an indicator which was present in the growth medium and which changes color when bacteria are present.

The invention being claimed is:

1. A process for joining thermoplastic closed-end tubes together transversely of the axis of each tube comprising (a) flattening a section of each tube to urge inside walls of each tube into contact, (b) urging a hot cutting means through the flattened section of each tube thereby temporarily sealing together the inside walls of each tube and providing molten tube ends, (c) aligning the tubes to be connected with each other, (d) joining the desired molten ends of said tubes together to form a joint between said tubes for each pair of tube ends to be connected, and (e) cooling each joint and then applying stress to each joint to open the temporary seal in each tube, thereby providing fluid communication between the joined tubes.

2. A process for forming a sterile connection between a first and a second closed-end tube, both formed of thermoplastic resin, comprising (a) mounting said tubes in a pair of mounting means which holds said tubes in a flattened, closely adjacent, substantially parallel position, (b) urging an edge of a hot cutting means having substantially flat surfaces through the flattened part of each said tubes at a rate such that the thermoplastic resin from which said tubes are formed and which is in contact with said cutting means becomes molten, thereby temporarily sealing together the inside walls of each tube and providing molten tube ends, (c) aligning said tubes with each other, (d) urging the desired molten tube ends together to form a joint between said tubes, and (e) cooling said joint and then applying stress to the joint to open the temporary seal in each tube, thereby providing fluid communication between the joined tubes.

3. A process according to claim 2 wherein the hot cutting means is maintained at a temperature above about 218° C.

4. A process according to claim 3 wherein the hot cutting means is maintained at a temperature below the temperature where the thermoplastic resin from which the tubes are made begins to degrade in the time used.

5. A process according to claim 4 wherein the mounting means holding the tubes is a pair of blocks having partial grooves therein which hold said tubes, said blocks providing the flattening of said tubes.

6. A process according to claim 4 wherein for step (e) the joint is cooled from about 1–3 seconds prior to applying stress to the joint.

7. A process according to claim 6 wherein the tubes to be joined are maintained in contact with the hot cutting means in step (c) and in step (d), are passed over an edge of the hot cutting means while said tubes are urged together.

8. A process according to claim 6 wherein the tubes to be joined are flattened in step (a) to an extent that fully-closed temporary seals are formed when the tubes and hot cutting means are separated.

9. A process according to claim 6 wherein the tubes to be joined are flattened in step (a) to an extent that fluid-tight temporary seals are formed in step (b).

10. A process according to claim 9 wherein, immediately prior to being flattened by the mounting means, the tubes are flattened with a clamp at the point where the hot cutting means passes, said process thereby providing sealed stub-ends.

11. A process according to claim 9 wherein the mounting means are spaced apart a distance such that the tubes to be joined are flattened to an extent that fluid-tight temporary seals are formed in step (b).

12. A process according to claim 9 wherein the tubes to be joined are removed from being in contact with the hot cutting means immediately prior to step (c).

13. An apparatus for forming a sterile connection between thermoplastic tubes comprising a cutting means, means adapted to heat said cutting means, a pair of mounting blocks adapted to receive, hold and flatten the tubes to be joined, means to provide movement between said blocks and said cutting means to a position such that the cutting means is between said blocks and traversing where the blocks are adapted to receive said tubes, means adapted to realign said blocks to a position where two different tube ends are aligned with and facing each other for each pair of tubes to be joined, means to separate said blocks and said cutting means, and means for urging said mounting blocks together.

14. An apparatus for forming a sterile connection between thermoplastic tubes comprising a cutting means; means adapted to heat said cutting means, a pair of mounting blocks adapted to receive, hold and flatten the tubes to be joined; means for movement of the mounting blocks to first, second and third positions, the cutting means being between the mounting blocks in the first position, said mounting blocks being relatively displaced in said second position to align two different tube ends facing each other for each pair of tubes to be joined, said mounting blocks being separated from said cutting means in said third position, and means for urging said mounting blocks together when in the third position.

15. An apparatus according to claim 14 wherein the means for urging the mounting blocks together is a spring.

16. An apparatus according to claim 13 wherein the means to provide movement between the cutting means and the mounting blocks, the means for realigning and the means for urging the blocks together are cam means which provide movement generating three orthogonal motions.

17. An apparatus according to claim 16 wherein the cam means is a driven cam cylinder containing one groove in each face and one groove around its periphery, one of said mounting blocks being coupled to the groove in one face of said cam and to the groove around the periphery of the cam, said cutting means being coupled to the groove in the other face of the cam cylinder, said apparatus having a controller coupled to the cam cylinder to control timing of operation of the apparatus.

18. An apparatus according to claim 13 or 14 wherein the mounting blocks comprise upper and lower portions hinged together, the inside surface of each upper portion being flat; partial grooves in said lower portions, said grooves serving to hold the tubes and beginning at a point removed from the proximal edge of each block and increasing in depth as the distal edge of each block is approached.

19. An apparatus according to claim 13 or 14 wherein the blocks are spaced apart from about 0.38 mm to about 4.2 mm.

20. An apparatus according to claim 19 wherein the blocks are spaced apart from about 0.38 to about 1.0 mm.

21. An apparatus according to claim 19 wherein the blocks are adapted to receive two tubes.

22. An apparatus according to claim 21 wherein the blocks are urged together after the cutting means and mounting blocks are separated.

23. An apparatus according to claim 19 wherein the blocks are adapted to receive three tubes.

24. A sterile connection system for continuous ambulatory peritoneal dialysis in which a dialysis solution container with a transfer port that includes a segment of tubing is coupled to a tube extending from a patient's peritoneal cavity, wherein the improvement comprises a pair of mounting blocks adapted to receive, hold and flatten the transfer port tube and the patient's tube, cutting means, means adapted to heat said cutting means, means to provide movement between said blocks and said cutting means to a position such that the cutting means is between said blocks and traversing where the blocks are adapted to receive said tubes, means to realign said blocks to a position where the resulting different tube ends to be joined are aligned with and facing each other, means to separate said blocks and said cutting means, and means for urging said blocks together.

25. A sterile connection system according to claim 24 wherein the blocks are urged together after the cutting means and blocks are separated.

26. The sterile connection system according to claim 25 wherein the patient's tube is connector-free and has a sealed distal end.

27. The sterile connection system according to claim 26 wherein the transfer port tube is connector-free has a sealed distal end, and is the same diameter as that of the patient's tube.

28. A sterile connection system for joining two blood bags, each bag having a tube which can be used for connection and sterile connection being made by joining said tubes, wherein the improvement comprises a pair of mounting blocks adapted to receive, hold and flatten the tubes to be joined; cutting means; means adapted to heat said cutting means; means to provide movement between said blocks and said cutting means to a position such that the cutting means is between said blocks and traversing where the blocks are adapted to receive said tubes; means to realign said blocks to a position where the resulting two different tube ends to be joined are aligned with and facing each other; means to separate said blocks and said cutting means; and means for urging said blocks together.

29. A sterile connection system according to claim 28 wherein the blocks are urged together after the cutting means and the blocks are separated.

30. The sterile connection system according to claim 29 wherein one of the bags is a donor bag and its blood collection tube is one of the tubes to be joined.

31. The sterile connection system according to claim 30 wherein the two tubes to be joined are of the same diameter.

32. The sterile connection system according to claim 31 wherein the blood collection tube has a sealed distal end.

33. The sterile connection system according to claim 32 wherein the second bag is a transfer bag having a transfer port with a transfer tube and the transfer tube is the other tube to be joined.

34. The sterile connection system according to claim 33 wherein the transfer tube has a sealed distal end.

35. The sterile connection system of claim 29 wherein one of the bags is a donor bag having, in addition to its blood collection tube, a connector-free tube to be used specifically for sterile connection, said tube having a sealed distal end.

36. The sterile connection system according to claim 35 wherein the donor bag is steam sterilizable and the other bag is a transfer bag made from material which is dry sterilizable only.

37. The sterile connection system according to claim 36 wherein the transfer bag has a connector-free tube having a sealed distal end.

38. The sterile connection system according to claim 37 wherein the two tubes to be connected are of the same diameter.

39. A sterile connection system for urinary drainage in which a first drainage container is connected to a drainage tube extended from a catheter implanted in a patient's urethra, wherein the improvement comprises (a) a second drainage container having a connector-free tube specifically for sterile connection and with a sealed distal end, both containers being disposable; and (b) a pair of mounting blocks adapted to receive, hold and flatten the drainage tube and the connector-free tube, cutting means, means adapted to heat said cutting means, means to provide movement between said blocks and said cutting means to a position such that the cutting means is between said blocks and traversing where the blocks are adapted to receive said tubes, means to realign said blocks to a position where the resulting different tube ends to be joined are aligned with and facing each other, means to separate said blocks and said cutting means, and means for urging said blocks together.

40. A reweldable connector system for continuous ambulatory peritoneal dialysis wherein a silastic catheter is surgically implanted in a patient's peritoneal cavity, comprising (a) said catheter, (b) a polyvinyl chloride tube optionally having a spike, (c) a thermoplastic connector tube having threaded ends, said connector tube being sterilely connected to said catheter on one end and to said polyvinyl chloride tube on the other end, (d) a polyvinyl chloride tube with a spike on one end and a connector tube portion on the other end, said connector tube portion being sealed on its distal end by fusion of its material, (e) a pair of mounting blocks adapted to receive, hold and flatten the thermoplastic connector tube and the thermoplastic connector tube portion, (f) a cutting means, (g) means adapted to heat said cutting means, (h) means to provide movement between said blocks and said cutting means to a position such that the cutting means is between said blocks and traversing where the blocks are adapted to receive said thermoplastic connector tube and said thermoplastic connector tube portion, means to realign said blocks to a position where different connector tube ends are aligned with and facing each other, means to separate said blocks and said cutting means, and means for urging said blocks together.

* * * * *